United States Patent [19]

Muto

[11] Patent Number: 4,685,472
[45] Date of Patent: Aug. 11, 1987

[54] SPECIMEN COLLECTOR

[75] Inventor: Rudolph Muto, 24 William St., Andover, Mass. 01810

[73] Assignee: Rudolph Muto, Lawrence, Mass.

[21] Appl. No.: 573,058

[22] Filed: Jan. 23, 1984

[51] Int. Cl.$^4$ ............................................. A61B 10/00
[52] U.S. Cl. ................................... 128/760; 210/446; 210/451; 604/190
[58] Field of Search ............... 128/758, 749, 756, 752, 128/762, 755, 760, 765; 210/321.3, 435, 446, 451, 470; 604/190, 191

[56] References Cited

U.S. PATENT DOCUMENTS

| | | | |
|---|---|---|---|
| 1,669,284 | 5/1928 | Chetham | 210/470 |
| 2,449,238 | 9/1948 | Lightfoot, Jr. | 210/155 |
| 3,002,870 | 10/1961 | Belgarde et al. | 210/446 |
| 3,214,025 | 10/1965 | Halpern | 210/250 |
| 3,512,940 | 5/1970 | Shapiro | 604/190 |
| 3,542,031 | 11/1970 | Taylor | 128/304 |
| 3,557,786 | 1/1971 | Barr et al. | 210/446 |
| 3,626,928 | 12/1971 | Barringer et al. | 604/264 |
| 3,735,751 | 5/1973 | Katz | 604/264 |
| 3,838,978 | 10/1974 | Eddleman et al. | 210/450 |
| 3,855,997 | 12/1974 | Sauer | 128/752 |
| 3,889,657 | 6/1975 | Baumgarten | 128/758 |
| 3,889,682 | 6/1975 | Denis et al. | 604/264 |
| 3,929,133 | 12/1975 | Ragab | 604/264 |
| 3,958,561 | 5/1976 | Bucalo | 128/262 |
| 4,083,706 | 4/1978 | Wiley | 55/385 R |
| 4,092,246 | 5/1978 | Kummer | 604/190 |
| 4,294,251 | 10/1981 | Greenwald et al. | 604/264 |
| 4,301,010 | 11/1981 | Eddleman et al. | 210/455 |
| 4,357,240 | 11/1982 | Mehra et al. | 210/455 |
| 4,393,879 | 7/1983 | Milgrom | 128/758 |

OTHER PUBLICATIONS

Gelman Sciences 81, *Laboratory Filtration Catalog*, p. 39, "OEC Wound Suction Systems", Orthopedic Equipment Company Commercial Literature.
Cotton, P. B. and Williams, C. B., *Practical Gastrointestinal Endoscopy*, (1982), p. 35.

*Primary Examiner*—William E. Kamm
*Attorney, Agent, or Firm*—Pearson & Pearson

[57] ABSTRACT

A specimen trap has first and second fluid chambers, an inlet tube for introducing fluid from the body into the first chamber, the walls of the trap defining a port substantially larger than the flow cross-section of the inlet tube for flow of fluid from the first chamber to the second chamber, and an outlet tube for removing fluid from the second chamber. The outlet tube projects into the second chamber and terminates therewithin at a position spaced from the walls of the chamber. When the chamber is turned to a position with outlet tube down, the outlet tube projection defines, with the second chamber, a fluid retaining volume in which a preselected minimum volume of collected fluid specimen is retained. A filter is disposed across the port to filter fluid flowing therethrough, and is supported at a position spaced from the outer walls defining the second chamber to inhibit back-flow of fluid through the filter that could resuspend the collected particles despite change in trap orientation. As normal flow through the trap proceeds, suspended particles can be isolated and a quantity of filtered liquid retained in close, humidifying relationship thereto, in a manner in which substantial resuspension of the isolated solid particles is inhibited despite change in orientation of the trap during handling prior to laboratory analysis of the specimen.

10 Claims, 7 Drawing Figures

SPECIMEN COLLECTOR

BACKGROUND OF THE INVENTION

The invention relates to collectors for use in medical suction lines for collecting specimens from the body for analysis. Such collectors are used during surgery as well as during cytological procedures. It has previously been common to collect a volume of fluid from the body and to separate the suspended tissue particles or cells at a later stage, in the laboratory. This method entails a risk of loss of the specimen by spillage during collection and subsequent handling and imposes a limit in the quantity of particles collected in cases where the volume of fluid containing the particles exceeds the volume of the collector. The laboratory separation step also has drawbacks because of personnel time, equipment and space required. Another prior approach has employed a flow-through filter upon which the particles of interest are deposited during collection. Such specimens can be dried and damaged due to absence of liquid for a period, for instance where the laboratory is busy or where for other reasons some period of delay occurs between collection and analysis. Prior techniques have generally also required close proximity between sites of collection and analysis.

For the reasons mentioned, any proposal to overcome these problems needs to avoid being complicated, expensive or cumbersome to use, should preserve sterility and should avoid damage to the particles of interest.

SUMMARY OF THE INVENTION

According to the invention, a specimen collector comprises first and second fluid chambers, an inlet tube for introducing fluid from the body into the first chamber, walls of the collector defining a port substantially larger than the flow cross-section of the inlet tube for flow of fluid from the first to the second chamber, an outlet tube for removing fluid from the second chamber projecting into the chamber and terminating therewithin at a position spaced from the walls, whereby, when the chamber is turned to a position with outlet tube down, the tube projection defines with the second chamber a fluid retaining volume in which a preselected quantity of collected fluid specimen is retained, a filtration means disposed across the port in a manner to filter fluid flowing from the first to the second chamber, the filtration means being supported at a position spaced from the walls defining the second chamber in a manner inhibiting back-flow of fluid through the filtration means that could substantially resuspend the collected particles during change in the orientation of the collector, whereby as normal flow through the collector proceeds, suspended particles can be isolated and a quantity of filtered liquid retained in close, humidifying relationship thereto, in a manner in which substantial resuspension of the isolated particles is inhibited despite change in collector orientation during handling prior to laboratory analysis of the specimen.

In preferred embodiments, the collector is adapted for in-line connection and has the inlet tube on one end, the outlet tube on the other end, and the first and second chambers aligned therebetween; the filtration means is smaller than the second chamber and is disposed closer to the outlet tube than is the end of the second chamber nearest the inlet whereby, during rotation of the collector to raise the outlet tube, fluid may move past in a path outward of the periphery of the filtration means and enter the portion of the second chamber closest to the inlet end of the collector without substantial exposure of the filtration means to contact with the fluid, and preferably the volume of the portion of the second chamber at the outlet end in which fluid collects when the outlet end is down is approximately equal to the volume of the portion of the second chamber closest to the inlet end in which fluid collects when the outlet end is up; an inward projection of the inlet tube is positioned closer to the filtration means than the inlet end of the first chamber, in position to direct fluid principally against the filtration means, preferably the first chamber into which the inlet tube discharges is defined by a tubular projection from a first end wall and the second chamber is defined by a tube of larger size surrounding the tubular projection and extending from the end wall to a second end wall spaced from the end of the tubular projection; the specimen collector further comprises a filter assembly extending across the port which is separable from the collector for removal of the collected particles, preferably the filter assembly is connected to wall portions defining the port and includes a hand grip to enable a technician to manually undo the connection and remove the filter assembly, more preferably the filter assembly is connected to the port by spaced apart, breakable bonds; and the port between the first and second chamber is defined by the end of a tubular projection and the filter assembly is of flat form, disposed across the end, preferably the collector is defined by a removable chamber-defining wall surrounding the tubular projection, adapted to be removed by the technician to expose the tubular projection and the filter assembly.

PREFERRED EMBODIMENT

We first briefly describe the drawings.

Drawings

STRUCTURE

Figure 1:
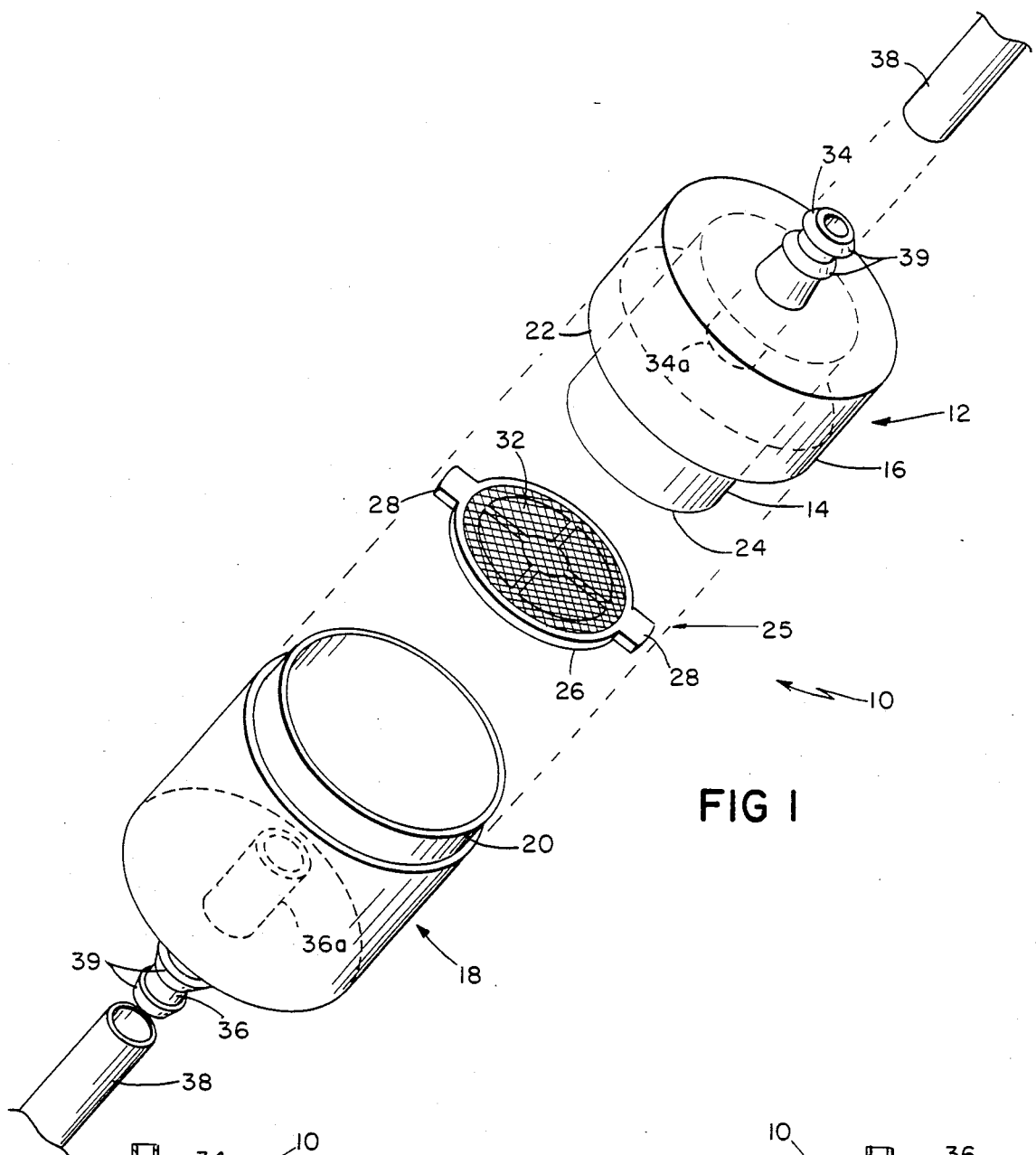
FIG. 1 is a perspective exploded view of a preferred embodiment of the specimen collector of the invention.

The collector 10, of clear plastic, is formed of portions 12 and 18 which fit together at a female-male connection. Female portion 12 has spaced apart inner and outer coaxial, generally cylindrical sections, 14, 16, and male portion 18 is of generally cylindrical shape, with a lipped rim 20 sized for liquid-tight friction fit inside rim 22 of cylinder 16 of female portion 12. Inlet and outlet conduits 34, 36 with ribbed, tube wall engaging projections 39 are respectively defined at the outer ends of portions 12 and 18 to provide for external connection to suction tubing 38. Extensions 34a and 36a of conduits 34 and 36 extend inwardly from the end walls of the trap for a significant length for purposes discussed below.

Inner cylinder 14 of portion 12 communicates with inlet 34 and extends axially beyond rim 22 to end 24 which forms a pedestal for filter assembly 25. This assembly is comprised of a ring-form filter retainer 26, matched in size to end 24, and flat filter medium 32.

Retainer 26 is bonded to end surface 24 at selected points 27 about the periphery. Tabs 28 extending from the body of retainer 26 facilitate gripping, twisting and breaking of the retainer from the pedestal after collection is complete, as discussed below. The inlet side surface 30 of retainer 26 supports filter medium 32, the periphery of the filter being bonded to respective circular ledges 27a the retainer, the filter medium thus having a drum-head-like orientation. For collection of cells the filter medium may, for instance, have openings in the range of 10 to 100 microns.

Outer cylinder 16 of portion 12 and the cylindrical wall of portion 18 bound a filtrate chamber 50, which not only provides a fluid path $P_1$ from the filter assembly to the outlet conduit 36, but also serves to define, with other structure of the trap, volumes $V_1$ (FIG. 5) and $V_2$ (FIG. 7) of approximately equal size.

Volume $V_1$, which is open to receive direct flow of filtrate, is an annular volume bounded also by the end wall of portion 18 and, at the center, by conduit extension 36a. (Thus length $L_1$ of extension 36a is a controlling dimension for the amount of liquid to be retained in volume $V_1$, in the preferred embodiment $L_1$ being equal to the radius of the cylindrical wall defining chamber 50).

Volume $V_2$, also an annular volume, is bounded by the end wall and inner cylindrical section 14 of portion 12. It also is open to receive filtrate, in this case by flow via annular path $P_2$ defined between the outer wall of the container and the edge of the smaller filter assembly 25 and its pedestal.

The size of inner cylinder 14 is determined by the desired ratio between flow cross-sectional area of the inlet 34a and the filter area. Typically this ratio is at least ten or substantially greater (depending upon type of particles and filter medium), to avoid a large pressure drop across the filter during build-up of deposit. In the preferred embodiment the conduits have flow diameter of 0.170 inch while the filter medium has a diameter of about one inch.

In the design of the preferred embodiment, given a desired one inch diameter filter and inner wall 14 and an outer wall of 1½" diameter, the length of cylinder 14 is a controlling dimension of volume $V_2$, and is selected so that the volume of $V_2$ is approximately equal to that of $V_1$.

The length of extension 34a of the inlet conduit is selected to define an appropriate path $P_3$ between the end of extension 34a and the filter medium 32 such that the fluid will be well-spread across the filter medium, while the exposure of the fluid to the interior side walls of cylinder 14 is limited.

Operation

Figure 3:
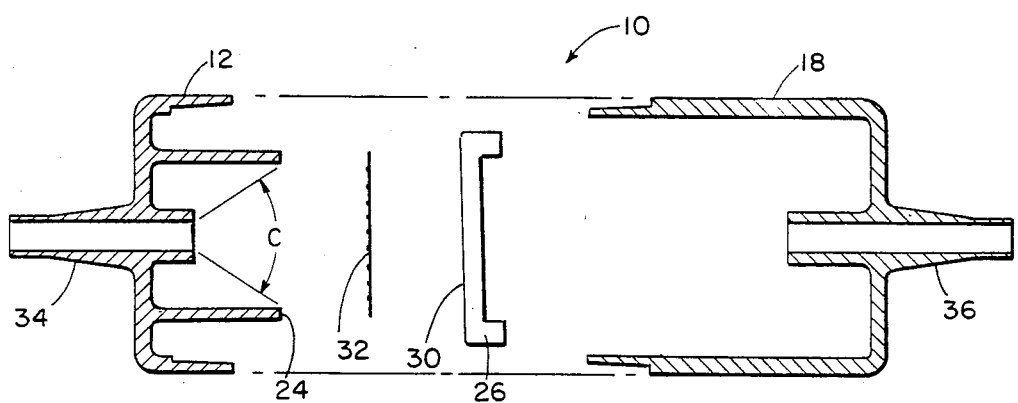
FIG. 3 is a similar view of the collector with the components separated.
Figure 4:
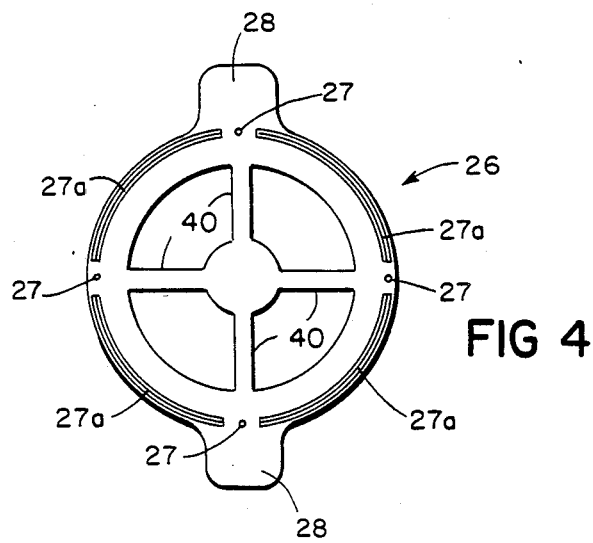
FIG. 4 is a plan view of the filter retainer.

Collector 10 is provided as a sterile, disposable unit with filter 32 affixed on the inlet side of retainer 26, and retainer 26 affixed on the pedestal end surface 24. The collector is installed in a suction line 38 that causes the liquid to flow from the body in the direction of the arrows A. By having the end of inlet conduit extension 34a within the collector positioned relative to the filter 32 to provide an exposure cone angle C (FIG. 3) of about 80 degrees, the fluid is directed onto the filter surface, and loss of specimen on the chamber walls is minimized. The surface area of the filter provides collection of particles without causing excessive pressure drop in the suction line, the pore size of the filter medium having been pre-selected for collection of the desired material without collection of smaller particles that would more quickly clog the filter.

Any pressure buildup that does occur across the filter as the particle specimens are collected has the effect of urging the male and female portions of the collector together, thus tightening the liquid seal of the two halves of the fluid container.

As particles suspended in the fluid are removed by filter 32, the filtrate passes between spider support arms 40 of retainer 26. Excess filtrate flows out of the collector via outlet conduit 36, while a substantial portion of it remains within the collector as a specimen.

Due to the construction of the collector, retention of a sufficient volume of liquid is assured despite variations in the orientation of the collector.

Figure 5:
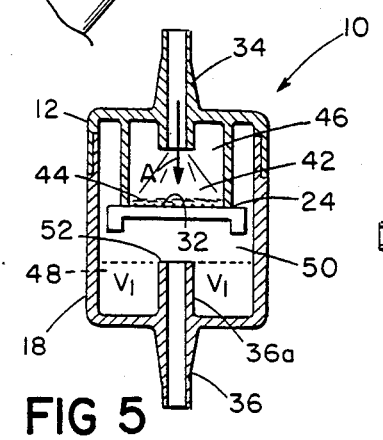
FIGS. 5, 6 and 7 are side section views showing fluid sample retention in different orientations of the collector.
Figure 6:
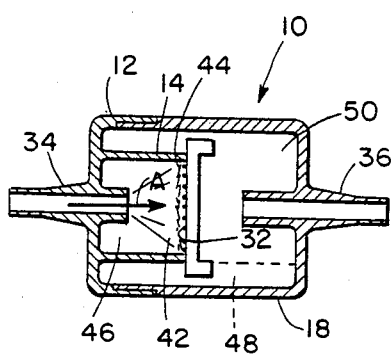
Figure 7:
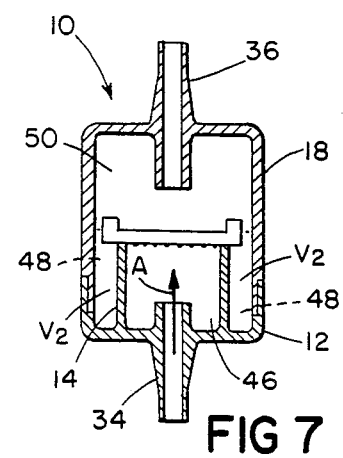
Figure 2:
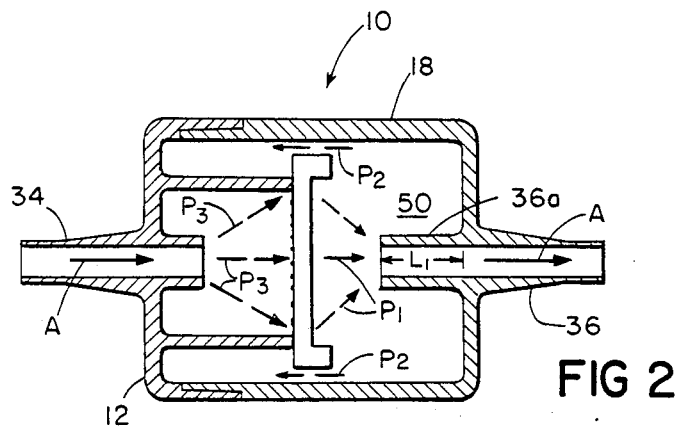
FIG. 2 is a side section view of the collector.

For example, referring to FIGS. 5 through 7, with the collector oriented with the outlet conduit 36 down (FIG. 5), fluid 42 from the body, containing suspended particles 44 enters the first chamber 46 (defined by the inner surfaces of cylindrical section 14, the end of the female inlet portion 12 and the filter 32) via inlet conduit 34 and is directed onto filter 32 positioned by pedestal 24. Particles 44 are collected on the filter, while the filtrate passes into the filtrate chamber 50 (defined by the inner surfaces of the female outer cylindrical section 16 of the female portion, the side and end surfaces of the male outlet portion 18, and the outer surface of inner cylindrical portion 14). Fluid 48 fills volume, $V_1$, corresponding to the volume of chamber 50 that lies below the opening 52 of outlet conduit 36.

In FIG. 6, the collector 10 is turned horizontally. Fluid 42 entering chamber 46 from inlet 34 is directed against filter 32 by the flow velocity created by the suction drawn on the collector through outlet conduit 36. Particles 44 are removed by filter 32. A volume of the fluid 48 is retained in chamber 50 while the excess is drawn out via conduit 36. In the horizontal orientation, a limited portion of filter 32 will be in contact with the collected liquid, however even in the worst case a sufficient portion of the solid specimen collected will be retained on the filter, and even when collection is ended, if fluid should flow each into the first chamber it will be retained due to the extended position of the inlet projection 34a.

Finally, in FIG. 7, the collector is shown oriented with the outlet conduit 36 at the top. In this orientation, body fluid entering chamber 46 from inlet 34 is directed against the filter and the fluid 48 is drawn through by suction. The fluid specimen collected in chamber 50 will be retained in the volume, $V_2$, lying outside of inner cylindrical portion 14 and generally below pedestal 24.

Referring still to FIGS. 5 through 7, the volumes $V_1$ and $V_2$ are predetermined so that if the orientation of the collector is changed, e.g. considering FIGS. 5, 6 and 7 as a sequence of movement, the fluid 48 in volume $V_1$ flows along the side wall of the trap (FIG. 6) via path $P_2$ radially beyond the pedestal 24 supporting filter 32 so that resuspension of the collected solid particles is substantially inhibited. Then, as the collector is oriented to the position in FIG. 7, the collected fluid flows into volume, $V_2$, so the fluid does not wash over the filter. Should some fluid flow back through the filter it will be retained in the first chamber.

When the collection procedure is completed, the ends of the collector may be sealed and the collector is removed to the laboratory for analysis of the specimens. The collection may even be performed in a remote location and the specimen sent to the laboratory by mail. Collection of the liquid and solid specimens at positions closely adjacent to one another within the same collector prevents deterioration of the collected tissue due to drying. Separation of the liquid and particle specimens during the collection procedure enables the laboratory technician to proceed immediately with the required analysis on both liquid and particles separately, without spending time to separate.

To remove the solid specimen, with the female potion on top the laboratory technician separates the male 18 and female 12 portions of the collector. Thus the filter and the male portion containing the collected liquid specimen are held upright. This exposes the filter assembly 25. The technician grasps tabs 28 of filter retainer 26 and by twisting lightly, breaks the spot bonds and removes the filter assembly. The solid specimen is then easily and quickly scraped from the flat, drum-head-like filter surface onto the specimen receiver without prolonged exposure to the air. The liquid specimen is easily removed by pouring from the male portion.

Numerous variations and other embodiments of the invention are possible within the spirit and scope of the following claims.

I claim:

1. A specimen collector comprising:
   a first liquid chamber comprising a first cylindrical liquid-impervious wall having an axis and two axial ends, a liquid-impervious end wall closing one axial end of the first chamber, and a filtration means attached transversely across the other axial end of the first chamber;
   an inlet conduit sealed to and leading axially into said first chamber from the end wall toward and terminating axially spaced from the filtration means, said conduit being spaced radially from the cylindrical side wall;
   a second liquid chamber comprising an outer cylindrical liquid-impervious wall of greater diameter than and coaxial with that of the first chamber cylindrical wall and having two axial ends, and a liquid-impervious end wall, at one axial end, the outer cylindrical wall liquid-imperviously joined to the one end wall of the first chamber, and a liquid-impervious end wall at the other axial end of the second chamber;
   there being an annular space surrounding the first cylindrical wall and the outer wall, the second chamber including and communicating with the annular space; and
   an outlet conduit sealed to and leading through and extending axially into the second chamber from the second chamber end wall toward and axially spaced from the filtration means, the outlet conduit extension being radially spaced from the outer wall to form with the outer wall and the second chamber's end wall an annular cup;
   whereby regardless of orientation during filtering of liquid from inlet to outlet conduits, the second chamber collects liquid and tends to inhibit back flow through the filtration means by retaining liquid in one of: the annular cup, the annular space, and along the outer wall; and whereby the annular cup may retain liquid filtrate when in upright orientation.

2. A specimen collector as claimed in claim 1, the cylindrical walls, and the inlet and outlet conduits being coaxially aligned.

3. A specimen collector as claimed in claim 1, the volume of the annular cup being approximately equal to the volume of the annular space.

4. A specimen collector as claimed in claim 3, the axial extension of the outlet conduit into the second chamber being approximately equal to the inner radius of the outer wall.

5. A specimen collector as claimed in claim 1, said filtration means comprising a filter retainer and a filter retained by the retainer closing the other axial end of the first chamber.

6. A specimen collector as claimed in claim 5, bonds at selected circumferential points of the filter attaching the filter to the filter retainer, said retainer having radially extending tabs for manual grip, whereby the retainer may be readily removed from the other axial end of the first chamber by twisting, turning at the tabs to preferentially break the bonds.

7. A specimen collector as claimed in 5, the filter retainer comprising circular ledges, the filter comprising a filter medium circular and flat in form, and bonds coupling the periphery of the medium to the ledges to form a drum-head like filter,.

8. A specimen collector as claimed in claim 1, said outer wall comprising two separable parts.

9. A speciment collector as claimed in 8, the said two parts being cylindrical, one of which has a lipped male rim, the other of which has a female rim, the rims being joined in male-female relation in a liquid-tight friction fit.

10. a specimen collector as claimed in claim 1, the solid angle between the axial termination of the inward extension of the inlet tube and the filtration means being approximately 80°.

* * * * *